United States Patent
Ohmori et al.

(10) Patent No.: US 6,291,482 B1
(45) Date of Patent: Sep. 18, 2001

(54) N-HYDROXYUREA DERIVATIVE AND PHARMACEUTICAL COMPOSITION CONTAINING THE SAME

(75) Inventors: Hiromasa Ohmori; Toshiya Komatsu; Michika Takano; Mina Tsuzuki; Yoshikazu Kawahara, all of Omiya (JP)

(73) Assignee: Nikken Chemicals Co., LTD, Tokyo (JP)

( * ) Notice: Subject to any disclaimer, the term of this patent is extended or adjusted under 35 U.S.C. 154(b) by 0 days.

(21) Appl. No.: 09/554,226

(22) PCT Filed: Nov. 9, 1998

(86) PCT No.: PCT/JP98/05034

§ 371 Date: May 11, 2000

§ 102(e) Date: May 11, 2000

(87) PCT Pub. No.: WO99/24426

PCT Pub. Date: May 20, 1999

(30) Foreign Application Priority Data

Nov. 11, 1997 (JP) .................................................... 9-323971

(51) Int. Cl.[7] .................................................. A61K 31/445
(52) U.S. Cl. ........................... 514/320; 514/456; 514/458
(58) Field of Search ............................................... 514/320

(56) References Cited

U.S. PATENT DOCUMENTS 5,300,518  4/1994  Okamoto et al. ..................... 514/338
5,356,921  10/1994  Ammann et al. ..................... 514/397

FOREIGN PATENT DOCUMENTS

| 2023016 A1 | * 2/1991 | (CA) . |
| 2023016 | 2/1991 | (CA) . |
| 58-15972 | 1/1983 | (JP) . |
| 05078321 | 3/1993 | (JP) . |
| 5-78321 | 3/1993 | (JP) . |
| 5-178855 | 7/1993 | (JP) . |
| 6-9571 | 1/1994 | (JP) . |
| WO 96/23772 | 8/1996 | (WO) . |

* cited by examiner

*Primary Examiner*—Dwayne C. Jones
(74) *Attorney, Agent, or Firm*—Christie, Parker & Hale, LLP

(57) ABSTRACT

A novel N-hydroxyurea derivative represented by formula (I) and having antiallergic and anti-inflammatory effects, i.e., N-hydroxy-N-[6-(3-pyridylmethyl)-2H-1-benzopyran-3-ylmethyl]urea:

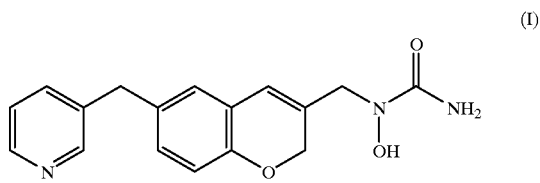

and medicines containing the above urea derivative or a pharmacologically acceptable salt thereof, or a hydrate or solvate thereof as the active ingredient, particularly antiallergic or anti-inflammatory agent, especially antiasthmatic.

6 Claims, No Drawings

N-HYDROXYUREA DERIVATIVE AND PHARMACEUTICAL COMPOSITION CONTAINING THE SAME

This application is a 371 of PCT/JP98/05034 filed on Nov. 9, 1998.

TECHNICAL FIELD

The present invention relates to novel N-hydroxyurea derivative having a lipoxygenase inhibitory activity and a thromboxane synthase inhibitory activity and pharmaceutical composition containing the same.

BACKGROUND ART

In recent years, the role of chemical mediators in asthma and other allergic diseases has been rapidly elucidated. In addition to histamine, PAF, leukotrienes, thromboxane, etc. have become known. It has been shown that leukotrienes are biosynthesized by the activity of 5-lipoxygenase from arachidonic acid, and thromboxane $A_2$ is biosynthesized by thromboxane synthase after the catabolism with cyclooxygenase from arachidonic acid. Further, both leukotrienes and thromboxane $A_2$ have been found to be important chemical mediators in allergic reactions, which cause various diseases such as asthma, chronic obstructive pulmonary disease, psoriasis, enteritis, nephritis, ulcers, and ischemia. Therefore, if it were possible to inhibit the biosynthesis of both chemical mediators, a greater effect could be obtained in treating or alleviating the above diseases when compared with the inhibition of single mediator.

Recently, as compounds for inhibiting the biosynthesis of such two mediators, benzothiazole derivatives (see Japanese Unexamined Patent Publication (Kokai) No. 5-178855), quinone derivatives (see Japanese Unexamined Patent Publication (Kokai) No. 5-78321), imidazolylphenol derivatives (see Japanese Unexamined Patent Publication (Kokai) No. 6-9571), and N-hydroxyurea derivatives (see WO96/23772) have become known.

DISCLOSURE OF THE INVENTION

The object of the present invention is to provide compounds capable of inhibiting the biosynthesis of both leukotrienes and thromboxane $A_2$, that is, novel compounds having both the dual inhibition against lipoxygenase and thromboxane synthase at the same time.

In accordance with the present invention, there are provided N-hydroxy-N-[6-(3-pyridylmethyl)-2H-1-benzopyran-3-ylmethyl]urea having the formula (I), and the salts thereof:

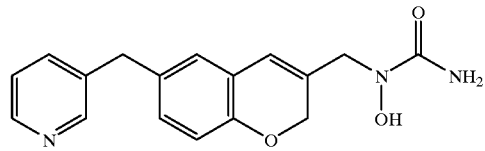

(I)

In accordance with the present invention, there is further provided a pharmaceutical composition comprising this N-hydroxy-N-[6-(3-pyridylmethyl)-2H-1-benzopyran-3-ylmethyl]urea or its pharmaceutically acceptable salts, or the hydrates or solvates thereof as an active component, in particular an antiallergic or anti-inflammatory drug, especially antiasthmatic.

BEST MODE FOR CARRYING OUT THE INVENTION

The present inventors widely studied to accomplish the above objects of the present invention. As a result, it was found that, among the compounds, which are included in the general wide concept, but not specifically disclosed in, for example, Examples, of benzopyran derivatives having a lipoxygenase inhibitory activity (Japanese Unexamined Patent Publication No. 3-83979), there are compounds having not only a lipoxygenase inhibitory activity but also a thromboxane synthase inhibitory activity. Thus, the present invention was completed.

Note that all the compounds having a lipoxygenase inhibitory activity disclosed in Japanese Unexamined Patent Publication No. 3-83979 do not possess the inhibitory activity of the thromboxane synthase and the present compounds are remarkably excellent, when compared with those compounds, for the purpose of curing or relaxing various diseases mentioned above.

The present invention will now be explained in further detail.

As mentioned above, the present invention provides N-hydroxy-N-[6-(3-pyridylmethyl)-2H-1-benzopyran-3-ylmethyl]urea and the salts thereof. As such a salt, the pharmacologically acceptable salts are preferable. The typical examples are salts of an inorganic acid such as hydrochloric acid, hydrobromic acid, sulfuric acid, bisulfuric acid, phosphoric acid, etc. and salts of an organic acid such as formic acid, acetic acid, oxalic acid, malonic acid, succinic acid, maleic acid, fumaric acid, citric acid, gluconic acid, lactic acid, tartaric acid, methanesulfonic acid, benzenesulfonic acid, toluenesulfonic acid, etc. Furthermore, the present invention includes the hydrates and solvates of the above-mentioned N-hydroxyurea derivatives and the salts thereof.

The N-hydroxyurea derivative according to the present invention can be produced by, for example, the following reaction formula (1) composed of the reaction steps 1–4, provided that the other method can be use for the synthesis thereof.

Reaction formula (1)

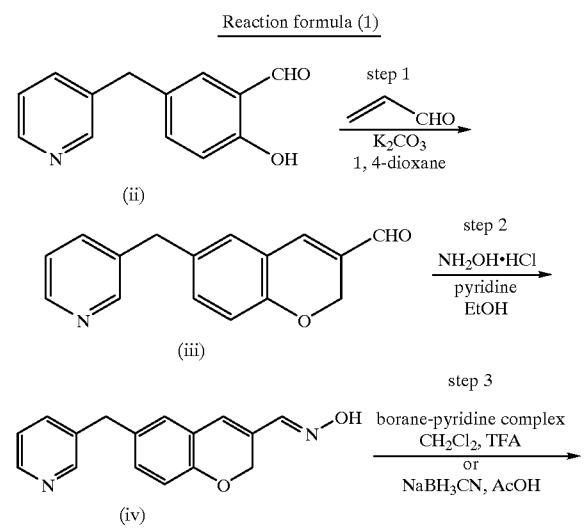

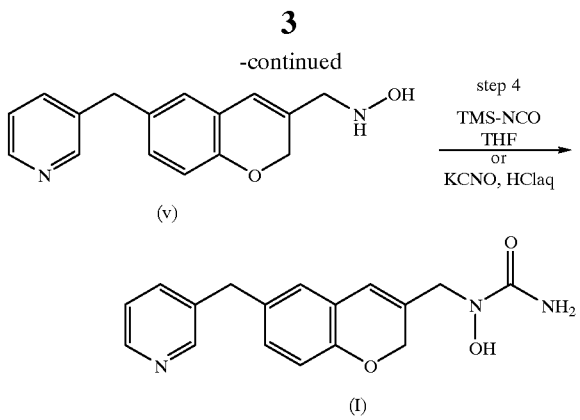

The starting substances used in the above reaction steps are those commercially available or those which may be produced from the known compounds by the known methods.

Step 1

3-(3'-Formyl-4'-hydroxybenzyl)pyridine (ii) is reacted, under a heating condition, with acrolein in the presence of an appropriate base such as potassium carbonate or sodium carbonate in a solvent, which does not inhibit this reaction, such as tetrahydrofuran or 1,4-dioxane to give the aldehyde (iii).

Step 2

The aldehyde (iii) is reacted with hydroxylamine hydrochloride in the presence of a base such as pyridine, picoline or triethyl amine in an appropriate solvent such as methanol, ethanol or propanol, or without a solvent, to give the oxime (iv).

Step 3

The oxime (iv) is reduced with an appropriate reductant to form hydroxylamine (v). As the reductant, borohydrides such as sodium cyanoborohydride or borane-amine complexes such as borane-pyridine complex, borane-dimethylamine complex are used. The reaction can be carried out under an acidic condition, namely in the presence of an appropriate acid such as an inorganic acid (e.g., diluted hydrochloric acid, diluted sulfuric acid) or an organic acid (e.g., formic acid, acetic acid, trifluoroacetic acid), with or without using an appropriate solvent such as an alcohol (e.g., methanol, ethanol), a halomethane (e.g., methylene chloride, chloroform), an ether (e.g., diethyl ether, tetrahydrofuran) to give the hydroxylamine (v).

Step 4

The hydroxylamine (v) is reacted with trimethylsilylisocyanate in a solvent, which does not inhibit this reaction, such as tetrahydrofuran, or is reacted with alkali cyanate such as potassium cyanate or sodium cyanate under an acidic condition such as, for example, a diluted hydrochloric acid or diluted sulfuric acid condition, to thereby give the desired N-hydroxyurea derivative (I). The N-hydroxyurea derivative (I) thus obtained can be preferably purified by known methods, alone or in any combination thereof, such as recrystallization, chromatography.

3-(3'-Formyl-4'-hydroxylbenzyl)pyridine (ii) to be used, as the starting compound, in step 1 is a known compound as disclosed in Japanese Unexamined Patent Publication No. 58-15972.

The compounds of the present invention may be administered by a suitable method of administration such as oral or non-oral administration when used as a drug for the treatment of allergic diseases or inflammatory diseases. As a form of oral administration, for example, tablets, granules, capsules, pills, powders, liquids, syrups, etc may be exemplified and, further, as a form of non-oral administration, injections, external application agents, inhalants, etc. may be exemplified. When preparing these medically administered compounds, the compound of the present invention or its pharmacologically acceptable salt may be prepared according to an ordinary method.

In the case of oral administration, the preparations can be prepared into the desired form using excipients such as lactose, glucose, corn starch, sucrose, a disintegrator such as calcium carboxymethylcellulose, hydroxypropylcellulose; a lubricant such as calcium stearate, magnesium stearate, talc, polyethylene glycol, hardened oil, a binder such as hydroxypropylcellulose, hydroxypropylmethylcellulose, carboxymethylcellulose, polyvinyl alcohol, gelatin, arabia gum, a humectant such as glycerin, ethylene glycol; and, in addition, surfactants, taste adjusters, etc., if necessary.

Further, in the case of a non-oral drug, a diluent such as water, ethanol, glycerin, propylene glycol, polyethylene glycol, agar, tragacanth gum may be used and solution adjuvants, buffer agents, preservatives, flavors, coloring agents, etc. may be optionally used.

When formulating the compounds of the present invention as drugs for the treatment of allergic diseases or inflammatory diseases, the dosage, as the compound of the present invention, is per adult, in the case of oral administration, 5 to 1000 mg per day, preferably 5 to 100 mg, and in the case of non-oral administration, 1 to 200 mg per day, preferably 1 to 20 mg. The desired effect of treatment can be expected by administration divided into one to three dosages per day. Furthermore, the present compounds have an NOAEL (i.e., non toxic level) of 100 mg/kg or more in a rat 14 days repeated toxicity test.

EXAMPLES

The present invention will now be explained, but is by no means limited to the following Examples:

Example 1

(1) Synthesis of 3-formyl-6-(3-pyridylmethyl)-2H-1-benzopyran 2.21 g of potassium carbonate and 2.20 ml of acrolein were added to a solution of 3.50 g (16.4 mmol) of 3-(3'-formyl-4'-hydroxybenzyl)pyridine in 1,4-dioxane (40 ml) and the mixture was heated at 100° C. for 30 minutes. Then, the resultant reaction mixture was filtered by using Celite (Trademark) and the filtrate was evaporated in vacuo. The residue was purified by a silica gel column chromatography (i.e., hexane: ethyl acetate=2:1 to 1:2) to obtain 3.88 g (yield=94.3%) of the desired compound as a yellow crystal.

$^1$H-NMR(CDCl$_3$): δ3.92(2H, s), 5.02(2H, s), 6.82(1H, d, J=8.3 Hz), 6.99(1H, d, J=2.0 Hz), 7.12(1H, dd, J=2.0, 8.3 Hz), 7.19(1H, s), 7.23(1H, dd, J=4.9, 7.8 Hz), 7.45–7.48(1H, m), 8.46–8.51(2H, m), 9.56(1H, s)

(2) Synthesis of 3-formyl-6-(3-pyridylmethyl)-2H-1-benzopyran oxime

Hydroxylamine hydrochloride was added to a mixed solution of 3.88 g (15.5 mmol) of 3-formyl-6-(3-pyridylmethyl)-2H-1-benzopyran in ethanol (35 ml) and pyridine (35 ml) at room temperature. The mixture was stirred for 2.5 hours was evaporated in vacuo and the residue was dispersed in chloroform-methanol (10:1). Then, after the organic layer was washed with water and brine, the solvent was evaporated in vacuo. The crystal precipitated during the evaporation of the solvent, was collected by filtration to obtain 3.46 g (yield=84.1%) of the desired compound.

$^1$H-NMR(DMSO-$d_6$): δ3.87(2H, s), 4.93(2H, s), 6.73–6.76(2H, m), 7.01–7.06(2H, m), 7.29(1H, dd, J=4.9, 7.8 Hz), 7.58–7.62(1H, m), 7.85(1H, s), 8.38–8.49(2H, m), 11.35(1H, s)

(3) Synthesis of N-[6-(3-pyridylmethyl)-2H-1-benzopyran-3-ylmethyl]hydroxylamine 13.1 ml of borane-pyridine complex was added dropwise to a mixture of 3.46 g (13.0 mmol) of 3-formyl-6-(3-pyridylmethyl)-2H-1-benzopyran oxime in methylene chloride (16 ml) and trifluoroacetic acid (16 ml) at −23° C. over 10 minutes and the mixture was stirred at the same temperature for 30 minutes, followed by addition of concentrated ammonia water to neutralize the acid. Then, water and an aqueous 10% sodium hydroxide solution were added to make the mixture basic, followed by extraction with ethyl acetate. After the organic layer was washed with water and brine, the solvent was evaporated in vacuo. The residue was purified by Florisil (Trademark) column chromatography (chloroform: methanol=50:1–15:1) to obtain 3.03 g (yield=86.9%) of the desired compound as an oil.

$^1$H-NMR(DMSO-$d_6$): δ3.41(2H, s), 3.84(2H, s), 4.72(2H, s), 6.33(1H, s), 6.66(1H, d, J=7.8 Hz), 6.87–6.96(2H, m), 7.29(1H, dd, J=4.9, 7.8 Hz), 7.39(1H, brs), 7.56–7.62(1H, m), 8.37–8.48(2H, m)

(4) Synthesis of N-hydroxy-N-[6-(3-pyridylmethyl)-2H-1-benzopyran-3-ylmethyl]urea (i.e., compound (I))

1.84 ml of trimethylsilyl isocyanate was added dropwise to a solution of 3.03 g (11.3 mmol) of N-[6-(3-pyridylmethyl)-2H-1-benzopyran-3-ylmethyl]hydroxylamine in tetrahydrofuran (30 ml) at 0° C. over 5 minutes, followed by stirring overnight at room temperature. Then, the solvent was evaporated in vacuo, the residue was purified by silica gel chromatography (chloroform:methanol:concentrated ammonia water=300:9:1–100:9:1), followed by recrystallization in a mixed solvent of chloroform-methanol-ethyl acetate to obtain 2.41 g (yield=68.5%) of the desired compound as white columnar crystal.

$^1$H-NMR(DMSO-$d_6$): δ3.84(2H, s), 4.03(2H, s), 4.66(2H, s), 6.33(1H, s), 6.44(2H, s), 6.68(1H, d, J=7.8 Hz), 6.90(1H, d, J=2.0 Hz), 6.95(1H, dd, J=2.0, 7.8 Hz), 7.29(1H, dd, J=4.9, 7.8 Hz), 7.56–7.61(1H, m), 8.39(1H, dd, J=2.0, 4.9 Hz), 8.48(1H, d, J=2.0 Hz), 9.40(1H, s)

Example 2
(Preparation of Tablets)

| | |
|---|---|
| Compound (I) | 250 g |
| Lactose | 620 g |
| Corn starch | 400 g |
| Hydroxypropyl cellulose | 20 g |
| Magnesium stearate | 10 g |

The above compound of the present invention, lactose, and corn starch were mixed until becoming homogeneous, then a 5 w/v % ethanol solution of hydroxypropyl cellulose was added and the mixture was mixed and granulated. The granules were graded by passing them through a 16 mesh sieve, then were formed into tablets by an ordinary method to form tablets of a weight per tablet of 130 mg, a diameter of 7 mm, and a content of the drug of 25 mg.

Example 3
(Preparation of Capsules)

| | |
|---|---|
| Compound (I) | 250 g |
| Lactose | 620 g |
| Abicel | 620 g |
| Magnesium stearate | 10 g |

The compound of the present invention, lactose, abicel, and magnesium stearate were sufficiently mixed until becoming homogeneous, then the mixture was filled into No. 3 capsules to obtain capsules of a weight per capsule of 150 mg and a content of the drug of 25 mg.

Test Example 1
(Test of Lipoxygenase Inhibitory Activity in In Vitro)

Using rat polymorphonuclear leukocytes, a test was conducted using as an indicator the amount of production of leukotriene $B_4$. SD male rats (Japan Clea) were intraperitoneally administered with 12% sodium casein. After 16 hours, the peritoneal cavities were lavaged and the polymorphonuclear leukocytes were recovered. The polymorphonuclear leukocytes thus obtained were suspended in a phosphate buffer (137 mM NaCl, 3 mM KCl, 8 mM $Na_2HPO_4$, 2 mM $KH_2PO_4$) ($2.5 \times 10^5$ cells/0.4 ml), then the test compound (final concentration $10^{-5}$M) was added and incubation performed for 10 minutes at 37° C. then a calcium solution (10 mM $CaCl_2$, 0.86% NaCl) 0.1 ml was added and incubation performed for 5 minutes, then 1.25 μl of calcium ionophore (20 μM, A-23187) was added and the reaction started. Five minutes after the addition, 250 μl of methanol was added to stop the reaction. After the reaction was stopped, the result was centrifuged for 20 minutes (4° C., 3000 rpm), then the amount of leukotriene $B_4$ in the supernatant was measured by the EIA method (Cayman Co. kit).

As the test compound, the compound (I) was used for the test. The inhibition of the production of leukotriene $B_4$ (LTBI) is shown in Table 1 by the $IC_{50}$.

Test Example 2
(Test of Thromboxane Synthase Inhibitory Activity in In Vitro)

Human platelet microsomes were used and a test performed using as an indicator the amount of production of the thromboxane $A_2$ stable metabolite thromboxane $B_2$. A buffer solution (20 mM tris-HCl buffer solution, 1 mM EDTA, pH 7.5) containing human platelet microsomes (50 μg protein/ml) and the test compound (final concentration of $10^{-6}$M) was stirred, then incubated at 0° C. for 30 minutes, followed by adding prostaglandin $H_2$ (100 ng/2 μl ). This was made acidic to stop the reaction, then neutralized with 1M Tris-base, then centrifuged at 3000 rpm for 20 minutes. The amount of the thromboxane $B_2$ in the supernatant was measured by the EIA method (Cayman Co. kit).

As the test compound, the compound (I) was used for the test. The activity of the compounds in inhibiting production of thromboxane $B_2$ (TxSI) is shown in Table 1 by the $IC_{50}$.

TABLE 1

| LTBI IC$_{50}$ ($\mu$M) | TxSI IC$_{50}$ ($\mu$M) |
|---|---|
| 0.2 | 0.3 |

Test Example 3
(Measurement of Lipoxygenase Inhibitory Activity and Thromboxane Synthase Inhibitory Activity in Ex Vivo)

For the test animals, SD male rats were used. These were made to fast from the day before the test. The test drug was suspended in 0.5% sodium carboxymethylcellulose and orally administered one hour before the blood was taken. The blood was taken from the abdominal aorta and divided for the measurement of the thromboxane synthase inhibitory activity and the 5-lipoxygenase inhibitory activity.

The 5-lipoxygenase activity was shown using as an indicator the amount of production of leukotriene $B_4$. 50 $\mu$M calcium ionophor (A-23187) was added to the divided blood to start the reaction (37° C., 30 minutes), and 1 mM Indomethacin, 1 mM Phenidone, and 0.1 mM EGTA were added to stop the reaction. The plasma was centrifuged (3000 rpm, 20 minutes, 4° C.) and the leukotriene $B_4$ in the plasma was measured by the EIA method.

As the test compounds, the present compound (I) and the compounds (A) and (B) below, which are disclosed in the Examples of the above-mentioned Japanese Unexamined Patent Publication No. 3-83979 were used and, as the 5-lipoxygenase inhibitory activity, the 50% inhibitory amount was calculated from the rate of inhibition of the test drug group with respect to the solvent control group (solvent: 5% gum arabic). The results are shown in Table 2.

On the other hand, the thromboxane synthase activity was shown using as an indicator the amount of production of the thromboxane $A_2$ stable metabolite thromboxane $B_2$. The divided blood was allowed to naturally coagulate (25° C., 90 minutes) and then the serum was centrifuged (3000 rpm, 20 minutes, 4° C.) and the amount of thromboxane $B_2$ in the serum was measured by the EIA method.

As the test compounds, the present compound (I) and the compounds (A) and (B) showed below, which are disclosed in the Examples of the above-mentioned Japanese Unexamined Patent Publication No. 3-83979 were used and, as the thromboxane synthase activity, the 50% inhibitory amount was calculated from the rate of inhibition of the test drug group with respect to the solvent control group (solvent: 5% gum arabic). The results are shown in Table 2.

(A)

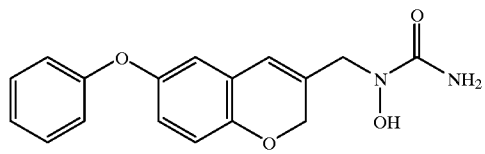

(B)

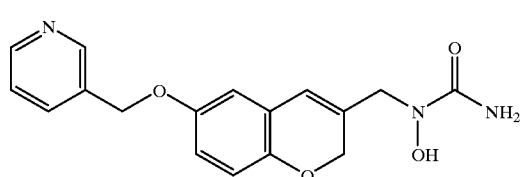

TABLE 2

| Compound | LTBI ED$_{50}$ (mg/kg) | TxSI ED$_{50}$ (mg/kg) |
|---|---|---|
| (I) | 1.7 | 1.5 |
| (A) | 1.7 | >30 |
| (B) | 9 | >10 |

As is clear from the above results of Table 2, the compounds disclosed in the Examples of the Japanese Unexamined Patent Publication No. 3-83979 has the lipoxygenase inhibitory activity, but does not have the thromboxane synthase inhibitory activity. Contrary to this, it is clear, that the present compound has the two activities of the lipoxygenase inhibitory activity and the thromboxane synthase inhibitory activity.

Test Example 4
(Pharmacological Activity on Antigen-Induced Bronchoconstriction Model of Guinea Pig)

Guinea pigs sensitized by ovalbumin were used and orally administered with the test compound suspended in 5% gum arabic. The activity for inhibiting antigen-induced bronchoconstriction after 2 hours after administration was measured by the Konzett-Rössler method.

Each of the sensitized guinea pigs (i.e., 5–7 pigs in one group) was anesthesized by 35 mg/kg pentobarbital, a cannula was inserted into the respiratory tract and connected to an artificial respirator, a cannula was inserted into the jugular vein, and treatment was performed by 5 mg/kg suxamethonium and 5 mg/kg mepyramine. Next, the guinea pig was inhaled a nebulized ovalbumin to cause bronchoconstriction and the activity in inhibiting bronchoconstriction was found from the ratio of the amount of overflow volume to the detector to the amount of air blown volume from the artificial respirator.

As the test compound, the present Compound (I) were used, and as the control, the above compound (A) and the thromboxane synthase inhibitor ozagrel hydrochloride (OKY-046) were used. The results are shown in Table 3 below.

TABLE 3

| | Amount administered (mg/kg) | Suppression rate of respiratory constriction (%) |
|---|---|---|
| Compound (I) | 50 | 75 |
| Compound (A) | 100 | 26 |
| OKY-046 | 100 | 42 |

From the results of Table 3, it is learned that the present compound exhibits the suppression rate of respiratory constriction higher than those of the control compounds, i.e., compound (A) and the commercially available drug OXY-046, regarding the antigen-induced respiratory constriction model of guinea pigs, and is useful as a drug.

INDUSTRIAL APPLICABILITY

The compound of the present invention has a strong inhibitory activity against lipoxygenase and thromboxane synthase, and also exhibits the strong respiratory constriction suppression action in the animal model, and therefore, is useful as a drug for treatment of allergic diseases or inflammatory diseases, more specifically, as a drug for the treatment or prevention of various diseases arising from the metabolites of arachidonic acid, for example, asthma, chyonic obstructive pulmonary disease, psoriasis, enteritis, nephritis, ischemia.

What is claimed is:

1. A thromboxane synthase inhibitory anti-inflammatory drug comprising N-hydroxy-N-[6-(3-pyridymethyl)-2H-1-benzopyran-3-ylmethyl]urea and having the formula (I):

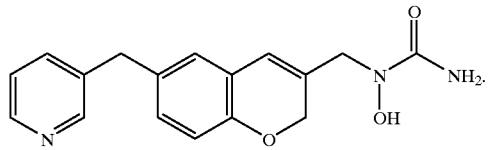

(I)

or its pharmacologically acceptable salt or the hydrate or solvate thereof and a pharmacologically acceptable carrier.

2. A thromboxane synthase inhibitory antiallergic drug comprising N-hydroxy-N-[6-(3-pyridymethyl)-2H-1-benzopyran-3-ylmethyl]urea and having the formula (I):

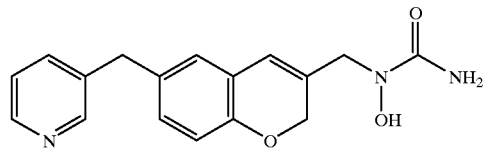

(I)

or its pharmacologically acceptable salt or the hydrate or solvate thereof and a pharmacologically acceptable carrier.

3. A thromboxane synthase inhibitory antiasthmatic drug comprising N-hydroxy-N-[6-(3-pyridymethyl)-2H-1-benzopyran-3-ylmethyl]urea and having the formula (I):

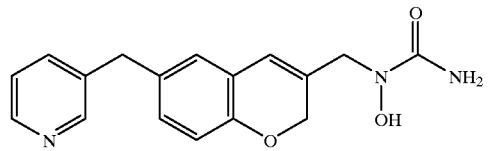

(I)

or its pharmacologically acceptable salt or the hydrate or solvate thereof and a pharmacologically acceptable carrier.

4. A thromboxane synthase inhibitory and lipoxygenase inhibitory anti-inflammatory drug comprising N-hydroxy-N-[6-(3-pyridymethyl)-2H-1-benzopyran-3-ylmethyl]urea and having the formula (I):

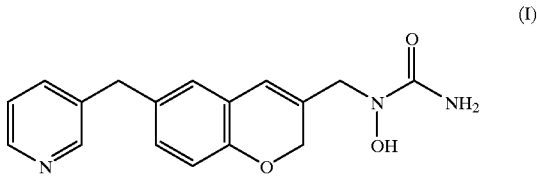

(I)

or its pharmacologically acceptable salt or the hydrate or solvate thereof and a pharmacologically acceptable carrier.

5. A thromboxane synthase inhibitory and lipoxygenase inhibitory antiallergic drug comprising N-hydroxy-N-[6-(3-pyridymethyl)-2H-1-benzopyran-3-ylmethyl]urea and having the formula (I):

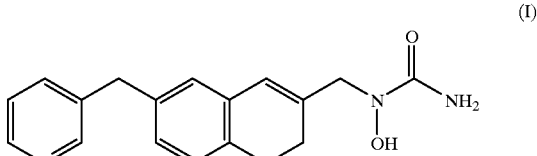

(I)

or its pharmacologically acceptable salt or the hydrate or solvate thereof and a pharmacologically acceptable carrier.

6. A thromboxane synthase inhibitory and lipoxygenase inhibitory antiasthmatic drug comprising N-hydroxy-N-[6-(3-pyridymethyl)-2H-1-benzopyran-3-ylmethyl]urea and having the formula (I):

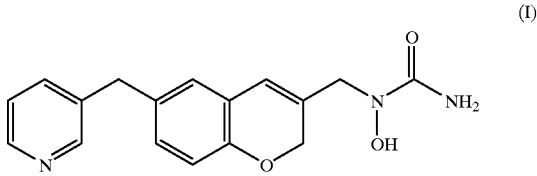

(I)

or its pharmacologically acceptable salt or the hydrate or solvate thereof and a pharmacologically acceptable carrier.

* * * * *